United States Patent
Lundy

(10) Patent No.: US 6,379,327 B2
(45) Date of Patent: Apr. 30, 2002

(54) HANDS-FREE PORTABLE BREAST PUMP SYSTEM

(76) Inventor: Ellen F. Lundy, 406 Seneca Ct., Woodstock, GA (US) 30188

( * ) Notice: Subject to any disclaimer, the term of this patent is extended or adjusted under 35 U.S.C. 154(b) by 0 days.

(21) Appl. No.: 09/843,113

(22) Filed: Apr. 25, 2001

Related U.S. Application Data

(62) Division of application No. 08/540,063, filed on Oct. 6, 1995.

(51) Int. Cl.[7] ................................................. A61M 1/06
(52) U.S. Cl. ......................................................... 604/74
(58) Field of Search ........................... 450/36–38; 2/67; 604/74–76, 343–346, 317; 119/14.12

(56) References Cited

U.S. PATENT DOCUMENTS

| | | | | |
|---|---|---|---|---|
| 22,018 A | * | 11/1858 | Davidson | |
| 22,080 A | * | 11/1858 | Lewis | |
| 2,054,491 A | * | 9/1936 | Tynan | |
| 2,436,430 A | * | 2/1948 | Hart | |
| 2,492,862 A | * | 12/1949 | Harvey | |
| 2,495,307 A | * | 1/1950 | Abrambson | |
| 2,516,129 A | * | 7/1950 | Leo et al. | |
| 2,585,338 A | * | 2/1952 | Meares | |
| 2,748,771 A | * | 6/1956 | Richards | |
| 2,764,759 A | * | 10/1956 | Gazelle | |
| 3,757,784 A | * | 9/1973 | Avery | |
| D246,729 S | * | 12/1977 | Murphy | |
| 4,270,538 A | * | 6/1981 | Murphy | |
| 4,311,141 A | * | 1/1982 | Diamond | |
| 4,335,728 A | * | 6/1982 | Fildan | |
| 4,566,458 A | * | 1/1986 | Weinberg | |
| 4,640,287 A | * | 2/1987 | Anderson et al. | |
| 4,673,388 A | * | 6/1987 | Schlensog et al. | |
| 4,680,028 A | * | 7/1987 | Stuart | |
| 4,705,504 A | * | 11/1987 | Viers | |
| 4,740,196 A | * | 4/1988 | Powell | |
| 4,878,879 A | * | 11/1989 | Kunstadter | |
| 5,032,103 A | * | 7/1991 | Larsson | |
| 5,071,403 A | * | 12/1991 | Larsson | |
| 5,514,166 A | * | 5/1996 | Silver et al. | |
| 5,571,084 A | * | 11/1996 | Palmer | |

OTHER PUBLICATIONS

The Natural Choice Company "Breast is Best", 1995—The Natural Choice Company, Inc, 1995.*
Packing Sheet: Ameda Egnell, one–hand breast pump/dual hygienikit™—,1994.*

* cited by examiner

Primary Examiner—Mark Bockelman
(74) Attorney, Agent, or Firm—Reed Smith Hazel & Thomas LLP

(57) ABSTRACT

A portable breast pump system that includes a breast receptor for receiving a breast, a vacuum suction compartment connected to the breast receptor and a collection container for receiving breast milk. The breast pump system also includes a breast milk collection tube having one end connected to the vacuum suction compartment and the other end connected to the collection container. The system also includes a suction pump connected to the breast receptor and the vacuum suction compartment for creating a vacuum for drawing breast milk into the collection container via the breast milk collection tube. Supporting the breast pump system in a portable manner on a mother are a breast receptor support strap for supporting and securing the breast receptor against the breast and a body strap for positioning on the body. The body strap has at least one retainer for portably holding the collection container or the suction pump.

18 Claims, 5 Drawing Sheets

HANDS-FREE PORTABLE BREAST PUMP SYSTEM

PRIORITY

This divisional application claims benefit of previously filed nonprovisional application Ser. No. 08/540,063 filed on Oct. 6, 1995 pending.

FIELD OF THE INVENTION

The present invention relates to breast pumping systems and, in particular, to portable breast pumping systems.

BACKGROUND OF THE INVENTION

It is believed by many nutritionists that breastfeeding is generally the best source of food and nutrition for an infant. Many experts and mothers believe that numerous immunological and nutritional advantages are provided by breast milk. Because of the benefits of breastfeeding, numerous breast pump devices have been developed which extract milk from a mother's breast for subsequent use when it is inconvenient for the mother to breastfeed the infant.

Although milk obtained by breast pump devices enables an infant to be conveniently fed at a later time, the act of using a breast pump to obtain the milk from the mother may cause the mother to be inconvenienced. Typically, it takes a mother approximately 10–20 minutes to obtain 2–6 ounces of milk to be used for feeding the infant. Because many mothers are "working moms," these mothers typically have many tasks to complete at home, including feeding their infants, in a short period of time. Due to the limited time that a mother has to complete daily obligations, taking time out to breast-feed during busy periods of the day can cause an additional inconvenience to the mother.

While breast pump devices enable a mother to conveniently provide breast milk to the infant without having to actually nurse the infant, breast pump devices require a mother to stop or delay a task at hand to spend time pumping her breast for milk. Prior breast pumps have a vacuum unit, milk container and breast receptacle all constructed as a single unit. With this single unit, the mother must generally sit and hold the breast pump to her breast for the amount of time that is required to extract the milk. Taking time out to sit or otherwise use her hands to hold the breast pump is inconvenient for a busy mother and usually requires the mother to delay accomplishing other tasks.

Thus, there is a need in the art to provide a breast pump system that enables a mother to conveniently collect milk without substantially encumbering or delaying the mother.

SUMMARY OF THE INVENTION

Generally described, the present invention provides a portable hands-free breast pumping system. The breast pumping system collects milk without the mother holding the breast pumping system in place while enabling the mother to perform other tasks unencumbered by the breast pumping system.

More particularly, the present invention provides a portable breast pump system for pumping the breast of a mother that includes a breast pump, a breast milk collection container, a breast receptor connected to the collection container and the breast pump, and a plurality of retaining straps for securing the breast receptor against a breast for collecting milk and for securing the breast milk collection container and the breast pump against the body of the mother. The breast pumping system is secured in a manner that allows the mother to move freely while milk is extracted from the breast without the mother holding the breast pumping system in position for pumping the breast during collection of milk from the breast.

Described in more detail, the present invention provides a portable breast pump system that includes a breast receptor for receiving a breast, a vacuum suction compartment connected to the breast receptor and a collection container for receiving breast milk. The breast pump system also includes a breast milk collection tube having one end connected to the vacuum suction compartment and the other end of the milk collection tube connected to the collection container. The breast pump system also includes a suction pump connected to the breast receptor and connected to the vacuum suction compartment for creating a vacuum for drawing breast milk into the collection container via the breast milk collection tube. Supporting the breast pump system in a portable manner on a mother are a breast receptor support strap for supporting and securing the breast receptor against the breast and a body strap for positioning on the body upon which the breast is located. The body strap has at least one retainer for portably holding the collection container or the suction pump on the body.

One of the retaining straps may be a breast receptor support bra, having at least one breast support cup. The breast receptor support cup may be adapted to hold the breast receptor in attachment to the breast. The breast support bra may have an opening defined therein for positioning the breast receptor through the opening. The breast receptor has an end for connection with a milk collection tube extending out from the opening in a direction away from the breast. The breast receptor support bra may further include an adjustment strap that has a plurality of position holders attached to the breast support cup. The position holders secure the breast receptor in selected positions in the breast support cup. The adjustment strap is preferably positioned across the opening defined in the breast receptor support bra.

The breast receptor support bra may include two breast support cups and have a second breast receptor for attachment to another breast. A second milk collection tube may be connected to the second breast receptor for drawing breast milk into the container via the second collection tube. Each breast receptor is separately contained in an individual breast support cup.

Additionally, one of the retaining straps may be a body strap for securing on the body upon which the breast is located. The body strap may portably hold the collection container or the suction pump on the body. Preferably, the body strap is a waist belt with pockets. Additionally, the present invention may include a refrigerated container for receiving the collection container and the refrigerated container may also be positioned in the body strap.

Another aspect of the present invention which is generally noted above is the breast receptor support bra. The breast receptor support bra includes a breast support cup. The breast support cup has an opening defined through the breast support cup for receiving a breast receptor of a breast pump. Attached to the breast support cup is an adjustment strap. The adjustment strap has a plurality of position holders attached to the breast support cup and the position holders secure the breast receptor in selected positions in the breast support cup. The breast receptor support bra includes a connection member which is connected to the breast support cup for supporting the breast support cup against the breast when the breast receptor is positioned between a breast and the breast support cup of the breast pump. The breast receptor support bra may include a second breast support cup. The second breast support cup may have an opening defined through the second breast support cup for receiving a second breast receptor of a breast pump.

Thus, it is an object of the present invention to provide a hands-free breast pumping system.

It is another object of the present invention to provide a breast pumping system which is fully portable and allows a mother to accomplish many tasks unencumbered by the breast pumping system.

It is another object of the present invention to provide retaining straps for supporting the breast pumping system on a mother in a comfortable manner.

It is another object of the present invention to provide a breast receptor support bra with an adjustable support for a breast receptor of the breast pumping system.

These and other objects, features, and advantages of the present invention will become apparent from reading the following description in conjunction with the accompanying drawings.

DETAILED DESCRIPTION

Figure 1:
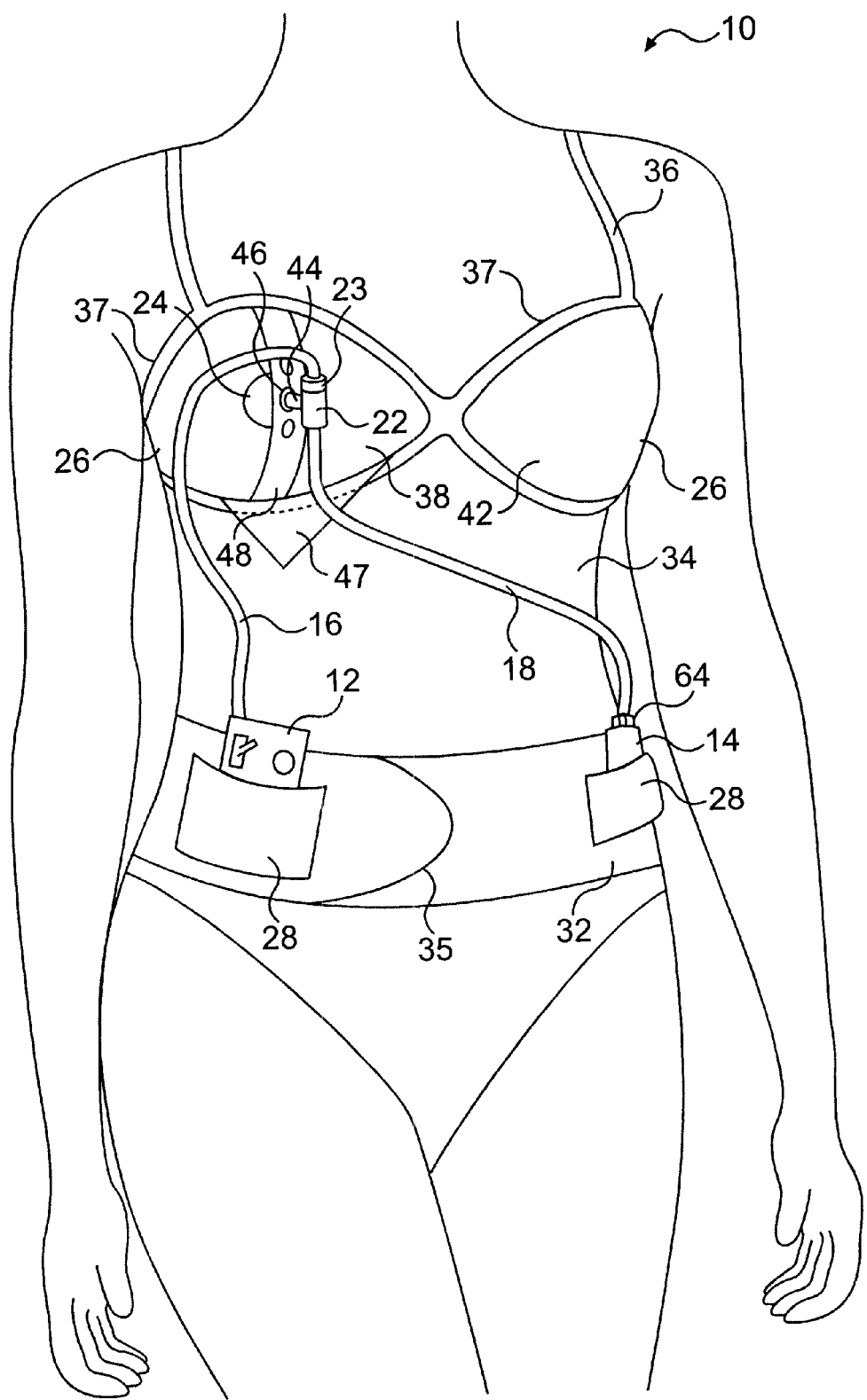
FIG. 1 shows the breast pumping system of the present invention.

Referring to the Figures, where like numerals reference like parts throughout the several views, the preferred embodiments of the present invention are discussed. Referring to FIG. 1, a breast pump system 10 includes a breast pump 12, a collection container 14, a vacuum tube 16, a collection tube 18, a vacuum compartment 22, a breast receptor 24, a receptor bra 36, and a waist belt 32. The vacuum tube 16 has one end connected to the breast pump 12 and the other end connected to the vacuum compartment 22 in order to provide suction at the breast receptor 24 for extracting breast milk from a breast 26. The collection tube 18 has one end connected to the vacuum compartment 22 and the other end connected to the collection container 14. The suction from the breast pump 12 causes breast milk to flow into compartment 22 which then drains down through collection tube 18 into collection bottle 14. A check valve or filter 23 is provided between vacuum tube 18 and the vacuum compartment 22 to prevent milk from flowing back through the vacuum tube 18 to the breast pump 12. As illustrated, the collection bottle 14 is located in a pocket 28 of the waist belt 32. Also, the breast pump 12 is located in a pocket 28 of waist belt 32. The breast receptor 24 is held in place against the breast 26 by the breast receptor support bra 36. The breast receptor support bra 36 has openings 38 defined therein that may be covered by a flap 42 of the lower portion of breast support cups 37. By providing the openings 38, the breast receptor 24 may be inserted within the receptor support bra 36 for securing the breast receptor 24 in a hands-free manner against the mother's breast 26. The breast receptor 24 has an extension 44 that extends through an opening 46 defined in an adjustment strap 48 of the receptor support bra 36 in order to connect with the vacuum compartment 22. The openings 46 in the adjustment strap 48 are spaced apart at selected distances in order that a mother may adjust the breast receptor 24 within the breast receptor support bra 36 to a more comfortable or more functional position.

Because the breast receptor 24, the breast pump 12 and the collection container 14 are all supported on the person's body or torso 34 by retaining devices or straps such as the waist belt 32 and the breast receptor support bra 36, the breast pump system 10 of the present invention is a hands-free breast pumping system which allows a mother to engage in other activities while breast milk is being extracted for subsequent use. The breast pump system 10 allows a mother to collect milk unencumbered without having to remain stationary at a pumping station and does not require the mother to manually hold the breast pump 12 or the breast receptors 24 in an appropriate position for collecting milk.

Figure 2:
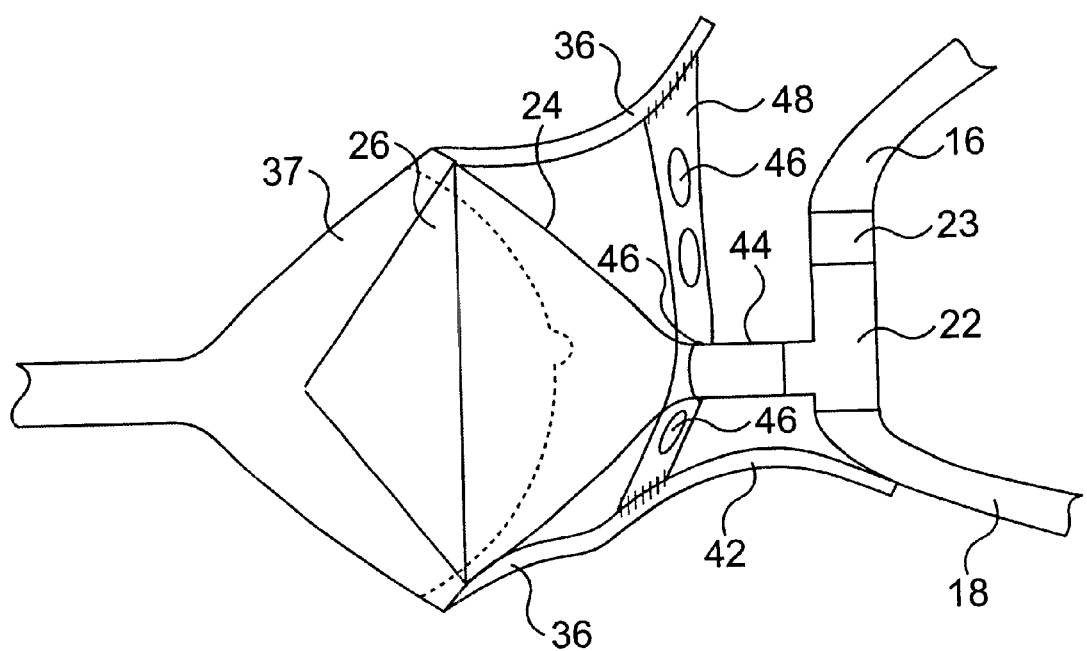
FIG. 2 shows a side view of a breast receptor support strap of the present invention and connections with other aspects of the breast pumping system.

Referring to FIG. 2, a side view of the breast receptor 24 and the breast receptor support bra 36 is shown. The structure of the breast support cups 37 of the breast receptor support bra 36 has the same general structure as a conventional nursing bra, however, the breast receptor support bra 36 further includes a strap or insert, the adjustment strap 48, for securing the breast receptor 24 in the breast support cup 37 in an appropriate position against a mother's breast. The adjustment strap 48 may be made of a cloth material or fabric that is sturdy enough to position the breast receptor 24 as desired. It should be appreciated that the adjustment strap 48 may be made of a flexible polymer material or other suitable materials. The material chosen for the adjustment strap 48 should be comfortable against the breast of a mother or should be a combination of materials with the material contacting the breast being suitably comfortable for the mother. The breast receptor 24 may be adjusted up and down by positioning the breast receptor extension 44 in any one of the openings 46 defined in adjustment strap 48. The adjustment strap 48 may have one end sewn to the upper portion of the breast support cup 37 and have the other end sewn to the lower portion of breast support cup 37. The adjustment straps 48 may be attached to the breast support cups 37 in any suitable manner known by those skilled in the art. The breast receptor 24 may be made of hard plastic as generally used in making conventional handheld breast pumps. The breast receptor 24 may also be made of soft silicone or rubber material which is comfortable to a normal adult female breast.

The breast receptor 24 has a large end which tapers down to a small end to form a conical shape. At the smaller end of the breast receptor is an extension 44 through which fluid, such as breast milk, may pass. The smaller end includes an opening through which the fluid may pass to the collection tube 18. The shape of the large end should be designed to comfortably fit or accommodate breasts of various sizes. The plastic or material forming the breast receptor 24 is preferably transparent to insure proper application to the nipple and areola which helps a mother avoid sore nipples caused by improper application of the receptor 24. Connected to the breast receptor 24 via the vacuum compartment 22 are the vacuum tube 18 and the collection tube 16. The vacuum tube 18 and the collection tube 16 are preferably cylindrical in shape and are made of a flexible material that has a thickness substantial enough to prevent the tube from collapsing under a reduction of internal air pressure when the vacuum is created by activation of the breast pump 12. Each of the tubes should snugly fit on the connecting devices in an airtight manner or a liquid-tight manner to prevent leakage during the pumping process. Each of the tubes 16 and 18 should be long enough and have enough flexibility to comfortably extend from the vacuum compartment 22 to waist belt 32 containing the breast pump 12 and collection container 14.

Figure 3:
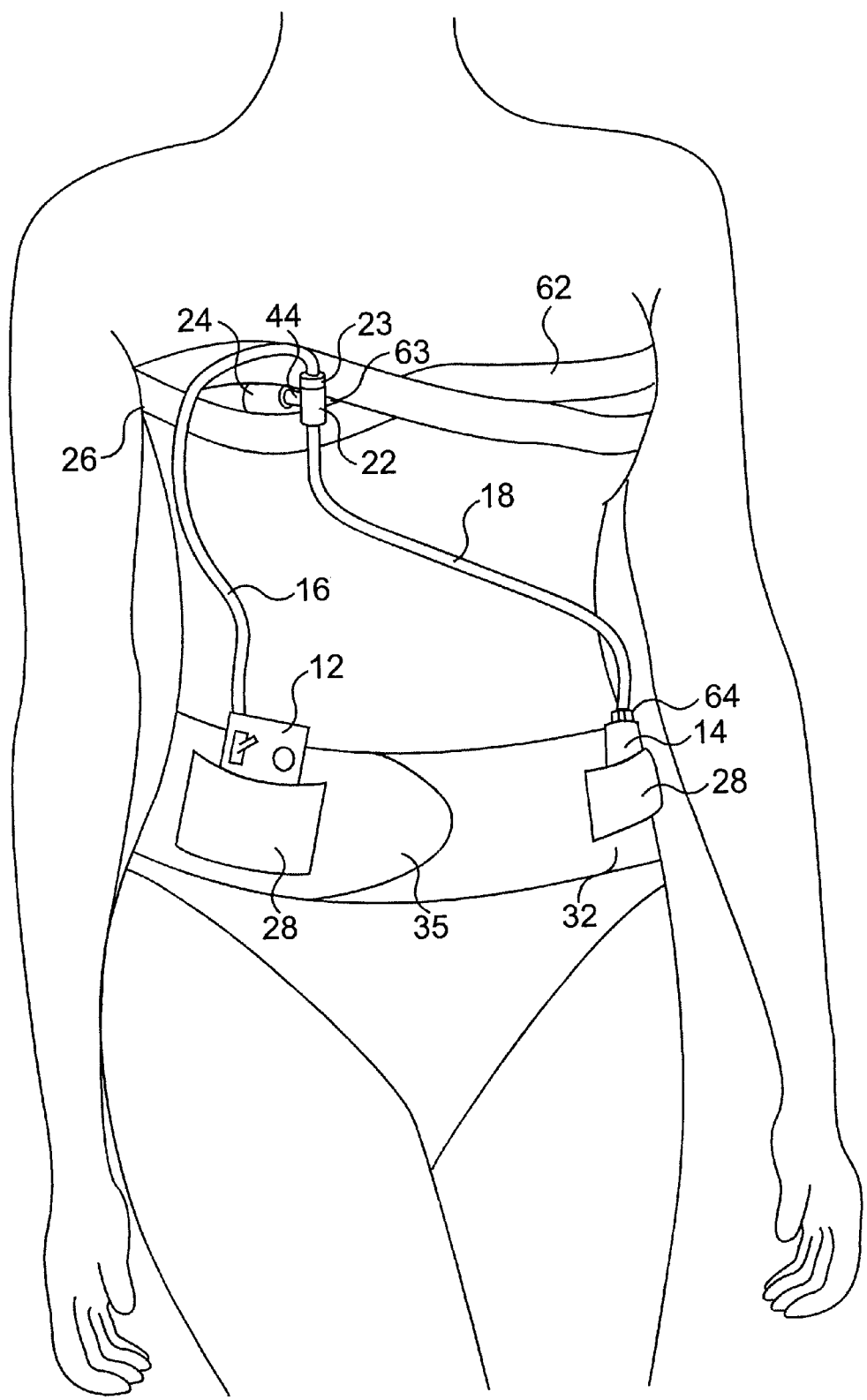
FIG. 3 shows another embodiment of breast receptor support strap used with the present invention.

Referring to FIG. 3, another embodiment of a receptor support strap is shown utilized with the present invention. The breast receptor 24 may be held in place by an adjustable receptor strap 62 which wraps around the upper torso of the mother. The adjustable receptor strap 62 has an opening 63 for receiving and supporting the breast receptor 24. The opening 63 may be sized to receive the extension 44 of the breast receptor 24 or the opening may be large enough to receive the conical portion of the breast receptor 24. When the opening is large enough to receive the conical portion of the breast receptor 24, the opening of adjustable strap 62 should be made of elastic-type material in order to support breast receptors of various sizes. The adjustable strap 62 may be made of flexible/breathable soft material, such as stretch nylon, with VELCRO® attachments or other suitable fasteners as known by those skilled in the art.

Referring to FIGS. 1 and 3, the waist belt 32 should be made of comfortable material such as nylon. As noted above, the waist belt 32 may fasten around the waist with VELCRO® attachments or any suitable fasteners. The waist belt 32 may be made of a woven textile material or any other suitable material. The pockets 28 of the waist belt 32 may be made of the same or material different from the material of the waist belt. It should be appreciated that pockets 28 are not the only means for securing or retaining the breast pump 12 or the collection bottle 14 to the waist belt 32. For example, the waist belt 32 may include retainers that hook into a slot on a breast pump 12 or collection bottle 14, the retainers may include a belt that slides through a loop on the breast pump 12 or collection bottle 14 or the retainers may be elastic bands which are strong enough to support either the breast pump 12 or the collection bottle 14 when placed between the elastic band and the waist belt 32.

The breast pump 12 may be a low vacuum suction pump operated by batteries or may be used with an AC adapter. A breast pump that 12 that may be used with the present invention is a small pump may be comfortably supported by or carried in the waist belt 32 which may be a back support belt such as available from orthopedic supply firms, for example, Best Orthopedic Products, Inc. of Hickory, N.C. The breast pump may comprise a normal vibration pressure/vacuum, an adjustable suction regulator, an adjustable cycle valve and a battery pack. Vacuum pressure should be adjustable and operate within a range from zero to 280 mm Hg. Adjustments to the vacuum suction of the pump can be made by adjusting the appropriate control on the vacuum or the vacuum line as known by those skilled in the art. The breast pump 12 may be operated on an intermittent basis simulating the suction of a newborn infant. The suction cycle may also be varied by adjustment of a control on the breast pump 12. The suction cycle is preferably from 0.5 seconds to 120 seconds. The breast pump 12 may also include a timer that cycles on and off at selected intervals. For example, the timer may cycle on or off every two to three hours.

The process of extracting milk from a mother's breast is as follows. When the suction pump 12 is turned on, a vacuum is created in the vacuum tube and up to the vacuum compartment 22. The vacuum created at the vacuum compartment 22 causes a vacuum or suction action through the breast receptor cup 24 when breast receptor cup 24 is in connection with breast 26. Upon the beginning of the suction at the breast 26, breast milk begins to flow through the vacuum compartment 22 and down through the collection tube 18 to the collection container 14. As discussed below, the collection container 14 may be enclosed in some form of refrigeration pack or ice pack to keep the breast milk refrigerated. When a mother has determined that enough breast milk has been collected, the mother may turn off the breast pump 12 and remove the collection tube 18 from the collection container 14 for storing the collection container 14 for later use.

Figure 4:
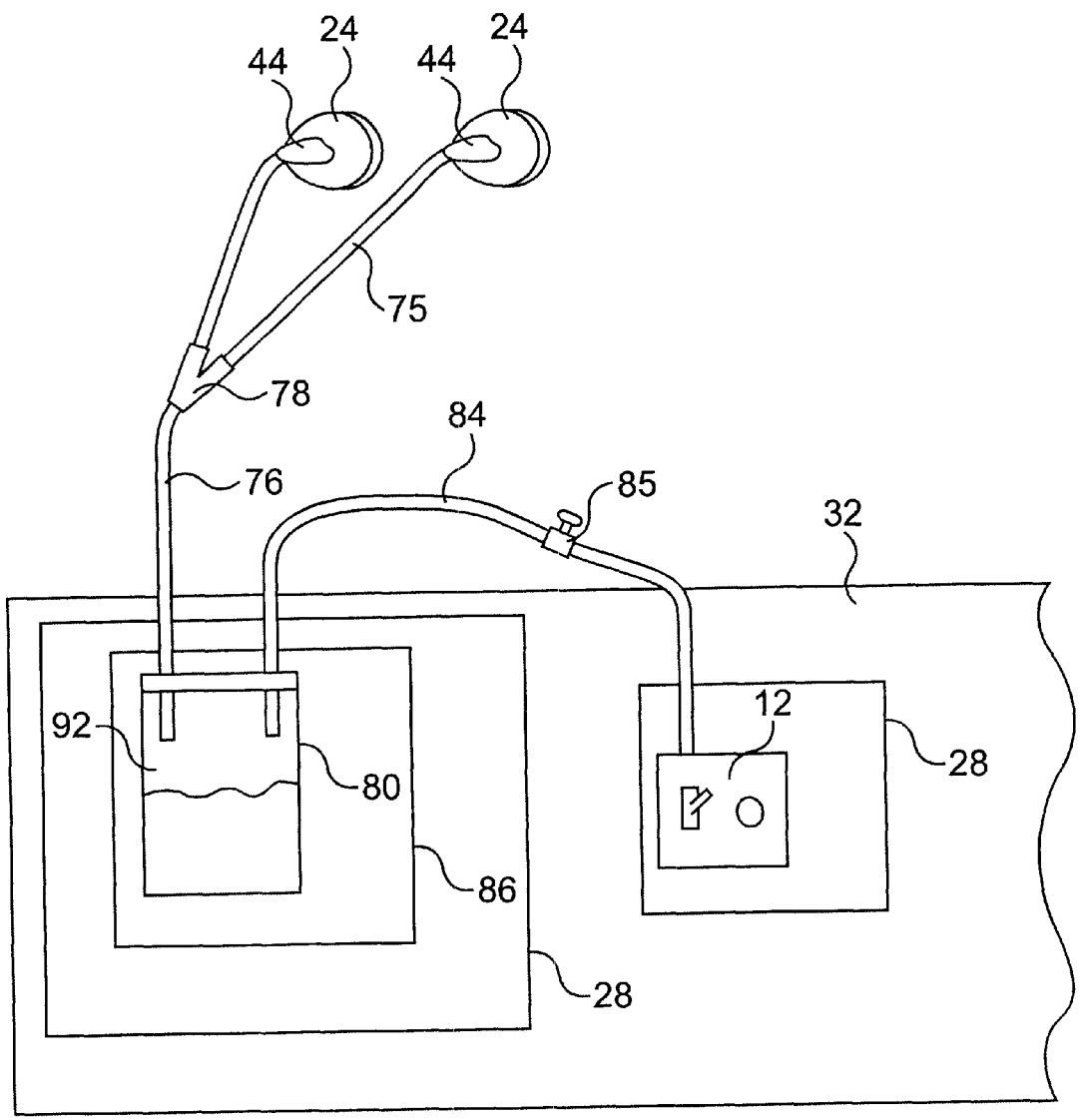
FIG. 4 shows another embodiment of the present invention in which two breast receptors are utilized.
Figure 5:
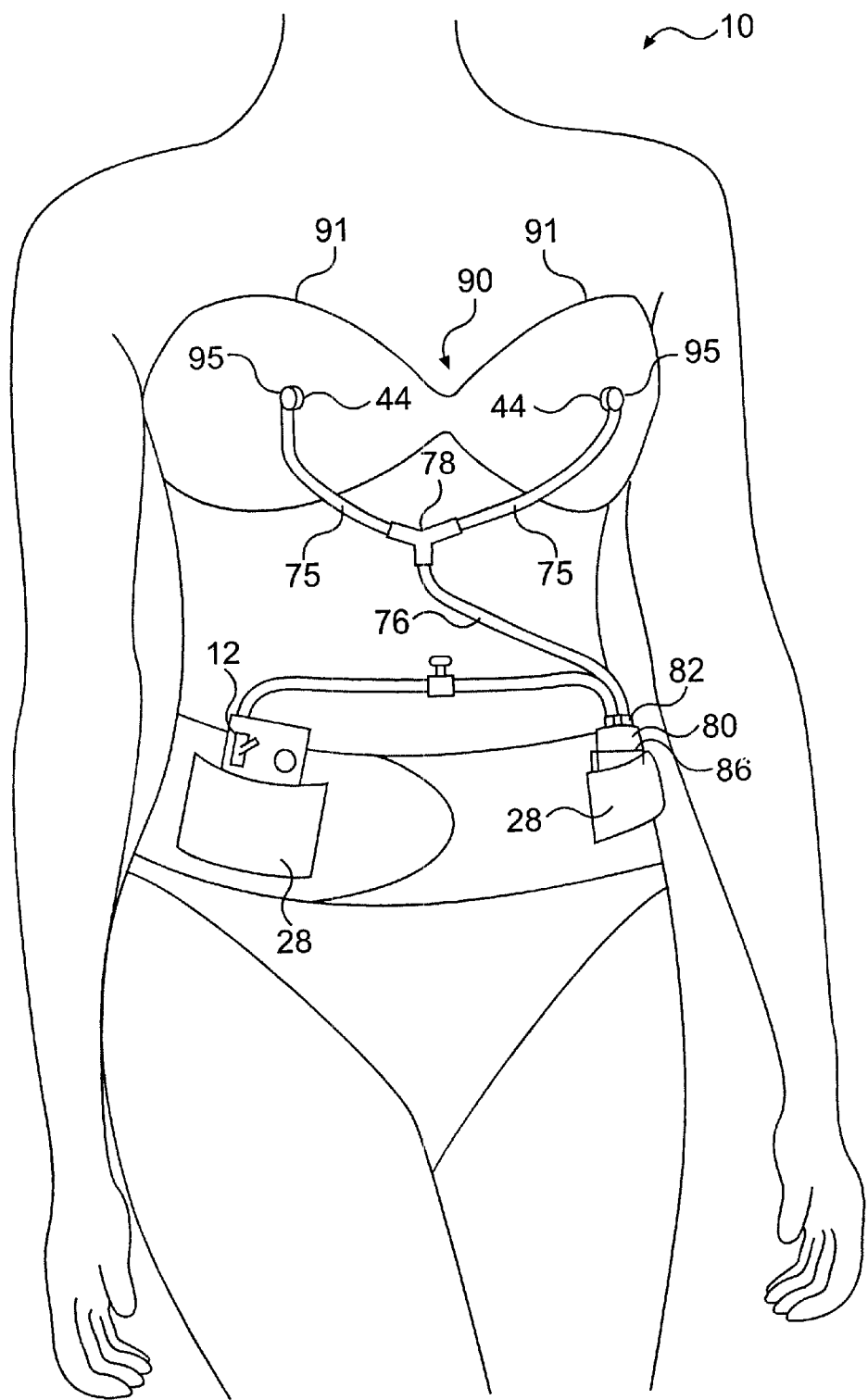
FIG. 5 shows the embodiment of FIG. 4 utilized with another embodiment of breast receptor strap of the present invention.

Referring to FIGS. 4 and 5, an alternate embodiment of the present invention shown. FIG. 4 shows two breast receptors 24 simultaneously coupled to the breast pumping system of the present invention. The breast receptors 24 may be positioned in the breast support cups 91 of a receptor support bra 90 as shown in FIG. 5. Each breast receptor 24 has one end of a collection tube 75 extending from the extensions 44 of the breast receptors 24. The other end of the collection tubes are connected to a "Y" connector 78 for channeling the milk from each breast down through collection tube 76 and into a collection container 80. The collection container 80 has a lid 82 through which the collection tube 76 is inserted. The collection container 80 may be housed in a refrigerated container 86 which includes ice or similar refrigerating media in order to refrigerate the milk during and after the collection process. Also, extending through the lid 82 of the collection container 80 is the vacuum tube 84 which is connected to the vacuum pump 12. By using the embodiment of FIG. 4, breast milk may be obtained from each breast simultaneously. By using the embodiment shown in FIGS. 4 and 5, more breast milk may be obtained in a shorter period of time. In the embodiment of FIG. 4, a vacuum is created in the area 92 within the collection container 80 when the vacuum pump is turned on. The vacuum created within the area 92 of the collection container 80 causes suction to be developed through the collection tubes 75, at the breast receptors 24 in order to extract milk from a mother's breast.

The breast receptor support bra 90 differs from the breast receptor support bra 36 in that single opening 95 is defined in each breast support cup 91 of the breast receptor support bra 90. The extension 44 of the breast receptors 24 are positioned through the openings 95 defined in the breast support cups 91. The breast receptor support bra 90 may have conventional fasteners, as discussed above, to hold the breast receptor support bra 90 in place.

By utilizing the breast receptor support straps of the present invention, a mother may accomplish many tasks with her hands which would not be otherwise possible if the mother had to hold the breast receptors and/or pump to her breast. Additionally, when the waist belt 32 of the present invention is utilized in conjunction with the breast receptor support bra of the present invention, an entirely portable and hands-free breast pumping system is provided.

The present invention is particularly useful to a mother who is unable to nurse her child due to reasons such as recovery from a "Cesarean" section, the child being born prematurely, illnesses which necessitate a need for intensive care and intravenous feedings, or when the mother is working and the infant is in daycare. Using the breast receptor support bra 36 to securely hold the breast receptors in place during the pumping process allows a mother to use the system overnight. By using this system overnight, the mother will be able to attach the breast pump system of the present invention before sleeping which allow the pump to work during the night. The pump may slowly extract or pump every ten to 120 seconds and may collect milk in a refrigerated unit or refrigerated ice chest as is shown in FIG. 4. During the day, the present invention allows the mother to collect breast milk virtually unencumbered by the breast pump system of the present invention.

The foregoing relates to the preferred embodiment of the present invention, and many changes may be made therein without departing from the scope of the invention as defined by the following claims.

What is claimed is:

1. A portable breast pump system, comprising:
   a breast receptor for receiving a breast;
   a vacuum suction compartment connected to said breast receptor;
   a collection container for receiving breast milk;
   a breast milk collection tube having one end connected to said vacuum suction compartment and the other end of said breast milk collection tube connected to said collection container;
   a suction pump connected to said breast receptor and connected to said vacuum suction compartment for creating a vacuum for drawing breast milk into said collection container via said breast milk collection tube;
   a breast receptor support strap for supporting and securing said breast receptor against said breast; and
   a body strap for positioning on the body upon which said breast is located, said body strap having at least one retainer, said retainer for portably holding said collection container and said suction pump on said body.

2. The apparatus of claim 1 wherein said breast receptor support strap comprises a breast receptor support bra, having at least one breast support cup, adapted to hold said breast receptor in attachment to said breast.

3. The apparatus of claim 2 wherein said breast support bra has an opening defined therein for positioning said breast receptor through said opening, said breast receptor having an end for connection with said breast milk collection tube extending out from said opening in a direction away from said breast.

4. The apparatus of claim 3 wherein said breast receptor support bra further comprises an adjustment strap having a plurality of position holders attached to said breast support cup, said position holders for securing said breast receptor in selected positions in said breast support cup.

5. The apparatus of claim 4 wherein said adjustment strap is positioned across said opening defined in said breast receptor support bra.

6. The apparatus of claim 2 wherein said breast receptor support bra comprises two breast support cups and said system further comprising a second breast receptor for attachment to another breast and a second tube connected to said second breast receptor for drawing breast milk into said container via said second tube, each of said breast receptors being contained in a separate one of said two breast support cups.

7. The apparatus of claim 1 further comprising a refrigerated container for receiving said collection container and said refrigerated container for positioning in a retainer of said body strap.

8. The apparatus of claim 1 wherein said body strap comprises a waist belt for positioning on the waist of said body.

9. The apparatus of claim 8 wherein said retainer comprises a pocket.

10. A portable breast pump system for pumping the breast of a mother, comprising:
    a breast pump assembly including a breast receptor and a pumping device;
    a breast milk collection container;
    said breast receptor connected to said collection container and said pumping device; and
    a plurality of retaining straps for securing said breast receptor against a breast for collecting milk from said breast and for securing said breast milk collection container and said pumping device against the body of said mother in a manner that allows said mother to move freely while milk is extracted from said breast without said mother holding said breast pumping system in position for pumping said breast during collection of milk from said breast.

11. The apparatus of claim 10 wherein one of said retaining straps comprises a breast receptor support bra, having at least one breast support cup, adapted to hold said breast receptor in attachment to said breast.

12. The apparatus of claim 11 wherein said breast support bra has an opening defined therein for positioning said breast receptor through said opening, said breast receptor having an end for connection with said collection container extending out from said opening in a direction away from said breast.

13. The apparatus of claim 12 wherein said breast receptor support bra further comprises an adjustment strap having a plurality of position holders attached to said breast support cup, said position holders for securing said breast receptor is selected positions in said breast support cup.

14. The apparatus of claim 13 wherein said adjustment strap is positioned across said opening defined in said breast support bra.

15. The apparatus of claim 11 wherein said breast receptor support bra comprises two breast support cups and said system further comprising a second breast receptor for attachment to another breast and a said second breast receptor connected to said breast milk collection container for drawing breast milk into said container via said second tube, each of said breast receptors being contained in a separate one of said two breast support cups.

16. The apparatus of claim 10 further comprising a refrigerated container for receiving said breast milk collection container and said refrigerated for positioning in a retainer of said body strap.

17. The apparatus of claim 10 wherein one of said retaining straps comprises a body strap for positioning on the body upon which said breast is located, said body strap having at least one retainer, said retainer for portably holding said collection container or said pumping device on said body.

18. The apparatus of claim 17 wherein said body strap comprises a waist belt for positioning on the waist of said body.

* * * * *